US007942388B2

(12) United States Patent
Suissa et al.

(10) Patent No.: US 7,942,388 B2
(45) Date of Patent: May 17, 2011

(54) MULTI-FRAGRANCE DIFFUSION DEVICE

(75) Inventors: David Suissa, Vincennes (FR); Clément Jeanjean, Paris (FR)

(73) Assignee: Conception et Valorisation de Brevets (CVB) (FR)

( * ) Notice: Subject to any disclaimer, the term of this patent is extended or adjusted under 35 U.S.C. 154(b) by 946 days.

(21) Appl. No.: 11/794,769

(22) PCT Filed: Jan. 5, 2006

(86) PCT No.: PCT/FR2006/000019
§ 371 (c)(1),
(2), (4) Date: Aug. 13, 2007

(87) PCT Pub. No.: WO2006/072744
PCT Pub. Date: Jul. 13, 2006

(65) Prior Publication Data
US 2008/0093474 A1 Apr. 24, 2008

(30) Foreign Application Priority Data
Jan. 5, 2005 (FR) ..................... 05 00079

(51) Int. Cl.
*B01F 3/04* (2006.01)
(52) U.S. Cl. ............... 261/30; 261/43; 261/45; 261/62; 261/DIG. 88; 239/59
(58) Field of Classification Search ............... 261/18.1, 261/30, 42, 43, 44.1, 45, 53, 62, 84, DIG. 65, 261/DIG. 88, DIG. 89; 239/58, 59, 60
See application file for complete search history.

(56) References Cited

U.S. PATENT DOCUMENTS

| 5,023,020 | A | * | 6/1991 | Machida et al. | ............. 261/18.1 |
| 5,167,877 | A | * | 12/1992 | Pai | ................................ 261/18.1 |
| 5,178,327 | A | | 1/1993 | Palamand et al. | |
| 5,259,062 | A | * | 11/1993 | Pelonis | ......................... 392/365 |
| 5,479,948 | A | * | 1/1996 | Counts et al. | ................. 131/194 |
| 5,565,148 | A | | 10/1996 | Pendergrass, Jr. | |
| 6,328,287 | B2 | * | 12/2001 | Wittek | ............................ 261/30 |
| 6,713,024 | B1 | * | 3/2004 | Arnell et al. | .................... 422/124 |
| 7,766,013 | B2 | * | 8/2010 | Wensley et al. | ........... 128/203.27 |
| 2002/0158351 | A1 | * | 10/2002 | Wohrle | ........................ 261/142 |
| 2003/0015196 | A1 | * | 1/2003 | Hodges et al. | ........... 128/203.16 |
| 2003/0015197 | A1 | * | 1/2003 | Hale et al. | ................ 128/203.16 |

FOREIGN PATENT DOCUMENTS

| DE | 100 44 894 A1 | 3/2002 |
| EP | 1 054 697 B1 | 11/2000 |
| EP | 1 212 104 B1 | 6/2002 |
| FR | 2 815 294 A1 | 4/2002 |
| WO | WO 2006/054031 A1 | 5/2006 |

* cited by examiner

*Primary Examiner* — Scott Bushey
(74) *Attorney, Agent, or Firm* — DLA Piper LLP (US)

(57) ABSTRACT

A scent diffusion device including an air flow generator; an outlet, the generator and outlet defining a path for the flow of air therebetween; a plurality of scent diffusion modules comprising: a slide moveable by sliding inside a housing between at least one diffusion position and a non-fragrant position; at least one first window in the slide intended to receive a source of fragrant molecules; a second window in the slide, wherein, in the diffusion position, the first window faces a window in the housing and in the non-fragrant position, the second window faces the window in the housing, and wherein the modules are positioned such that window axes of the housings of different modules are aligned on the path; and a device permitting the slides to be brought individually onto one of the positions; the flow of air successively traversing the windows of the housings, the first window and the second window of the slides according to positions of the latter.

23 Claims, 5 Drawing Sheets

MULTI-FRAGRANCE DIFFUSION DEVICE

RELATED APPLICATION

This is a §371 of International Application No. PCT/FR2006/000019, with an international filing date of Jan. 5, 2006 (WO 2006/072744 A1, published Jul. 13, 2006), which is based on French Patent Application No. 05/00079, filed Jan. 5, 2005.

TECHNICAL FIELD

This disclosure relates to the area of the diffusion of scents, more particularly, to a process and an electronically driven device for the diffusion of one or several scent(s). It is particularly adapted to perfume volumes with the dimension of an average-size hall, that is, whose surface is comprised between 20 and 100 square meters.

BACKGROUND

Various techniques for the diffusion of scents are known. The most current one uses materials drenched with fragrant molecules that are freed into the atmosphere by natural convection. This technique is largely used to perfume the passenger spaces of automobiles, for example. A better efficacy of the convection can be obtained by forcing the circulation of a flow of air making contact with the drenched material. In this instance, the flow of air is generally created by an electric turbine. Another current technique consists of burning a perfumed candle or a material such as incense. The strong heat produced by the combustion accelerates freeing the fragrant molecules. Finally, scent devices use the technique of micronization of an olfactory liquid that consists of diffusing the latter into fine droplets that vaporize rapidly, freeing the fragrant molecules. This technique is the one generally used to perfume large spaces such as train station concourses, for example.

Whatever the technique used by the scent diffusion device, it is always appropriate to re-drench or replace a material drenched with fragrant molecules when it has dried out, or to refill or replace a bottle containing a fragrant liquid when it has become empty.

Certain scent diffusers are driven by an electronic device. EP 01212104B1 describes a device for the diffusion of perfume based on a flow of air making contact with a drenched material, which device is driven by a digital television station or by a microcomputer. EP 01054697B1 discloses a device permitting the diffusion of several perfumes with the particularity of avoiding a persistence during a change of scent by virtue of a capacity of hermetic obturation of the perfume reservoirs that are not to be diffused. It describes a reservoir with a totally spherical form that is turned a quarter turn to place or not place the fragrant material in a flow of air.

Also, U.S. Pat. No. 5,565,148 teaches a device for the diffusion of scents having an air circulation corridor in the middle of which a barrel has a scent support. The air circulating in the corridor traverses the support, taking the fragrant molecules along with it.

The disadvantage of the solutions in which the scent supports are arranged on cylindrical, barrel-type supports resides in the fact that the passage from one scent to another is laborious and time-consuming, especially if the two supports are opposed in the barrel. This sometimes requires several seconds.

Also, FR 2 815 294 teaches a device for heating/air conditioning automobiles comprising elements of olfactory diffusion. An envelope comprising passages of air is arranged in the path of the air, inside of which a support slides to position an aromatic agent facing the passages. This solution is limited to a limited number of scents to be operational. Moreover, the solution has significant charge losses on account of the eccentric position of the envelope relative to the path of the air flow.

The following are also known: cartridges of liquid perfume activated by a device with arms in order to permit it to be opened, and the evaporation of molecules (US 2002/0158351) of the scent cartridges constituted by a material that is porous or similar to a sponge for imprisoning the fragrant molecules (U.S. Pat. No. 5,565,148), cartridges inserted in an opening made on a scent diffusion device, which cartridges are constituted by gel or drenched with sweet-smelling substances (DE 100 44 894), and cylindrical cartridges constituted by a rigid structure with cylinder quarters suitable for receiving olfactory substances (U.S. Pat. No. 5,178,327).

The prior art does not provide electrically driven multi-scent devices to be conceived that are simultaneously simple in design, modular and readily rechargeable. It could therefore be advantageous to provide multi-scent devices that require only a single electric turbine whatever the number of scents to be diffused, and that present a single diffuser orifice.

SUMMARY

We provide a scent diffusion device including means for generating a flow of air; an outlet, the generating means and outlet defining a path for the flow of air therebetween; and a plurality of scent diffusion modules including a slide moveable by sliding inside a housing between at least one diffusion position and a non-fragrant position; at least one first window in the slide intended to receive a source of fragrant molecules; a second window in the slide; wherein, in the diffusion position, the first window faces a window in the housing and in the non-fragrant position, the second window faces the window in the housing, wherein the modules are positioned such that window axes of the housings of different modules are aligned on the path; and means permitting the slides to be brought individually onto one of the positions, the flow of air successively traversing the windows of the housings, the first window and the second window of the slides according to positions of the latter.

We also provide a modular unit for the device including $2^i$ scent diffusion modules (i is a whole number from 1 to 3) arranged in a rigid structure with each module including a slide that can move by sliding inside a housing between at least one diffusion position and one non-fragrant position; at least one first window in the slide and adapted to receive a source of fragrant molecules; a second window in the slide wherein, in the diffusion position, the first window faces a window in the housing and in the non-fragrant position, the second window faces the window; wherein these modules are positioned in such a manner that axes of the windows of the housings of the different modules are aligned; and the rigid structure cooperates with means for receiving the device in such a manner that the windows are aligned with an air conduit.

We further provide a process for diffusion of scents using the device, including inserting scent cartridges inside the windows of the modules, creating a flow of air with the means for producing a flow of air, which flow of air traverses the set of windows of the housings, and placing at least a first window in front of the window such that flow of air traversing the windows also traverses the scent cartridge contained in the first window, which diffuses its scent.

We still further provide a cartridge or materials drenched with volatile fragrant molecules, adapted to be inserted in the windows of the devices, including two opposing surfaces designed to allow free passage to a flow of air while holding the materials, a thickness that is perceptibly less than that of the slide to permit the slide to freely slide in the housing including when the cartridge is in place in the window of the slide, a shape that substantially matches that of the window such that the totality of the flow of air traversing the window traverses the cartridge and a dimension in width that is slightly greater than that of the window such that the cartridge can be inserted and removed with a slight force by the elasticity of the cartridge.

BRIEF DESCRIPTION OF THE DRAWINGS

Our structures will be explained making reference to attached FIGS. 1 to 10 that present designs for a mono-scent device and a multi-scent device, in which.

DETAILED DESCRIPTION

Figure 1:
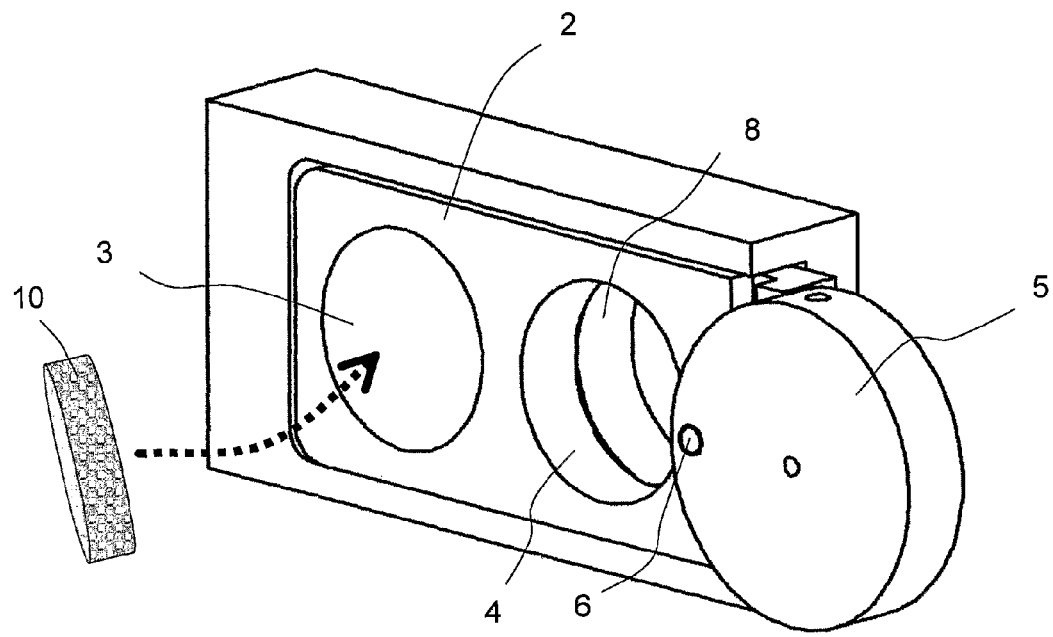
FIG. 1 shows a diffusion module for a scent in the non-diffusing position of scent.

We provide a device that diffuses a supplementary scent simply by adding a module to a design that has already been realized. The invention additionally intends to facilitate the recharging or the replacing of the fragrant materials once they have dried out by using readily replaceable cartridges. These advantages as well as others that will appear from a reading of the following description that render our devices particularly adapted for diffusing several scents into halls of an average dimension, between 20 and 100 m², whereas the state of the art addresses itself essentially to the perfuming of either smaller volumes such as the passenger space of a vehicle or of larger volumes such as train station concourses, most frequently by means of a single scent.

We provide devices for the diffusion of one or several scents from one or several materials drenched with fragrant volatile molecules in contact with a circulating flow of air. In the case of a multi-scent diffusion, the device is composed of a plurality of identical modules, one module for one or several scents to be diffused, and an electrical turbine generating a flow of air. The diffusion or stopping of the diffusion of a scent as well as the choice of the diffused scent are electronically controlled. Our devices permit the ready re-drenching or replacing of the fragrant materials once they have dried out by using removable cartridges that can be readily replaced or recharged. It avoids the persistence of a scent at the end of its diffusion as well as the spontaneous drying out of fragrant cartridges by positioning the cartridges from which the user does not wish to diffuse the scent in a hermetic enclosure.

To this end, we provide, in its most general meaning, a scent diffusion device comprising:

means for generating a flow of air and an outlet, which generating means and outlet define a path for the flow of air between themselves;

a plurality of scent diffusion modules comprising:
- a slide that can move by sliding inside a housing between at least one diffusion position and a non-fragrant position;
- at least one first window made in the slide intended to receive a source of fragrant molecules;
- a second window made in the slide;
- in the diffusion position the first window faces a window made in the housing;
- in the non-fragrant position the second window faces the window made in the housing;
- the modules are positioned in such a manner that the window axes of the housings of different modules are aligned on the path;
- means permitting the slides to be brought individually onto one of these positions;
- the flow of air successively traversing the windows of the housings as well as the first and second windows of the slides according to the positions of the latter.

The path of the flow of air between the means for generating the flow of air and the outlet can be realized by using delimiting walls, e.g., a pipe. The term "aligned" means that the axes of the windows of the housings (that is, the axis traversing the flow of air) are substantially parallel to the tangent of the flow of air at the location where the module is implanted. This parallelism favorably implies an angle of at least 30° between the window axes and the tangent. In particular, an angle of at least 10° is to be selected. Furthermore, the modules are arranged to center the windows of the housing on the central axis of the path and therefore these windows of the housings are fully traversed by the flow of air.

The using of scent modules is advantageous in that it allows a large number of modules to be readily linked to diffuse numerous scents. In this regard, we permit an efficacious modular solution to be provided where the prior art remains limited to a restricted number of compartments (e.g., number of elements of a barrel). The linear linking of the "lego" type allows only a single dimension (the length) to be increased to increase the number of scents while keeping constant the height and the width of the multi-scent diffusion device in contrast, e.g., to a cylindrical barrel. The modularity also permits easy substitutions of modules and/or frequent changes (heavy consumption or a need for new scents).

The presence of blowing means, ventilator or electrical turbine type, has the advantage of rapidly and precisely diffusing the scents in contrast to solutions based on convection by heating, that are subjected to a process of non-guided diffusion in the atmosphere. Thus, the user rapidly smells the scents.

Such a solution is also very economical as concerns the number of diffusible scents due to the use of similar modules (thus economies of scale) and of a single source of the flow of air.

In one aspect, the path has walls forming a corridor of air and these windows of these modules are aligned in the air corridor. Thus, the solution appears compact: a single entry point for air and a single outlet point are necessary for all the scents. This permits in particular a very directive use of the scents and does not oblige the user to move to smell another scent. This is especially practical for the diffusion of scents during video games or videos when the user is seated.

The corridor or air is perceived as a set of walls that efficiently delimit the path traversed by the flow of air. Such a corridor can be used via a tube or by several tube sections. For example, a first tube section guides the flow of air between the air generation means and a first module, a second section guides the flow of air that has traversed the module to a second module, etc. for the set of modules arranged in the air path, and finally a last tube section guides the flow of air exiting from the last module (after having traversed the set of modules of the diffusion device) to the device outlet.

The presence of the corridor for the purposes of confining and guiding the flow of air allows the charge losses of the flow of air to be considerably reduced.

In particular, the windows have substantially the dimension of the section of the air corridor (at least 50%, preferably between 70 and 100% of the corridor section) and are oriented substantially perpendicularly to the axis of the corridor. In this configuration, use of the flow of air is optimized to capture the maximum number of fragrant molecules.

To furnish great compactness and a tightness of the molecules among themselves, they are juxtaposed housing against housing.

According to different structures:
the means permitting the displacement of the slides are activated by an electric control part,
the device comprises a plurality of means permitting the movement of the slides and each of the plurality of means is individually associated with one of the plurality of modules for the diffusion of scents. In particular, the means permitting the movement of the slide is a servomotor whose stator is integral with the housing and whose rotor is integral with an eccentric finger that cooperates with a groove formed in the slide.

The use of electric controls (via an electronic card and an electronic drive) impart a great ability to the device for rapidly changing scents and retaining a constant speed in order to pass from one scent to the other in contrast to prior solutions, e.g., for scents arranged in a rotatable cylinder. For example, with 8 scents it is necessary to make 4 rotations from one scent to the scent situated physically opposite on the cylinder, which requires approximately four times the time necessary to pass from one scent to an adjacent scent.

The electronic driving card or the program driving this card can receive parameters from the user determining in the driving strategy, e.g., the size of the room to be perfumed. To this end a parallel or series connection (USB—Universal Serial Bus, RS232 or another) can equip the electronic card for parameterizing its drive from an external control source.

According to one aspect, each of the housings has in the aggregate a U shape inside of which the slide associated with the housing is inserted and slides.

To guarantee tightness of the modules and, thus, reduce the useless drying out of the cartridges, each module not having a neighbor on the face where the cartridge is visible comprises a plate suitable for shutting the source in a manner inaccessible to air when the slide is in such a position that the second window is facing the housing window.

During maintenance operations (changing of module or of cartridge, for example) the modules can be manipulated. To prevent the slides from being moved at the wrong time, the modules that are removable furthermore comprise means for blocking the slides in the non-fragrant position when they are not inserted in the device. The latter then comprises means for unblocking these blocking means when the removable module is inserted in the device.

These modules may comprise means for the storage of data (an electronic chip of the SIM or RFID card type or a barcode) comprising at least digital data representative of information concerning the sources of fragrant molecules that they contain, and the device furthermore comprises means for reading the data storage means, which reading means are connected to an electronic card for driving the device.

If desired, the source of fragrant molecules is a removable cartridge drenched with fragrant molecules. The cartridge comprises data storage means comprising at least digital data representative of the scent contained in the cartridge, and the device may further comprise means for reading the data storage means, which reading means are connected to an electronic card for driving the device.

The presence of such electronic chips is advantageous as it allows the processing unit (electronic card) to have information essential for the smooth functioning of the device. The information relative to the nature of the scent contained in each cartridge to efficiently control the appropriate actuators (servomotors) and also the information relative to the drying state of the cartridges (or their use) to adapt the flow of air required to ensure a constant scent in time and to indicate, if necessary, the changing of a cartridge are noted. It is thus possible to finely control the diffusion of the scents as a function of the olfactory performances of the nose in the image of the content of PCT/FR05/050968.

The means for generating a flow of air are selected from a ventilator and an air turbine according to the embodiment selected.

To compensate for a large corridor of air and the inevitable charge losses, it can be provided that the device furthermore comprises means for the acceleration of the flow of air arranged in the air corridor and driven by an electronic card for driving the device.

The device can also furthermore comprise means for adapting the output of the flow of air at the outlet of the air corridor. An electric air turbine can be used for this effect and permits the parameters of the output of the flow of air to be controlled, especially for managing the distance to which the perfumed molecules are sent. The turbine at the entrance of the air corridor permits, for its part, the managing of the quantity of perfumed molecules taken from the cartridges. These turbines are driven by the electronic card in accordance with the parameters entered by the user (size of the room, for example).

It is also provided that the slide of at least one module furthermore comprises at least a third window designed to receive a second source of fragrant molecules, which means allows the slide to be moved and is then suitable for bringing the slide to one of the at least three positions corresponding to the alignment of a window of the slide with the housing window. The number of diffusible scents can be considerably increased. Such slides with three or more windows are useful for frequently used scents for which the cartridges should be frequently changed. The electronic driving card is informed with the aid of electronic chips of the necessity of driving the servomotors in an adequate manner to position the slide in the three possible positions.

We also provide a modular unit for a device, comprising $2^i$ scent diffusion modules (i is a whole number from 1 to 3) arranged in a rigid structure with each module comprising:
a slide that can move by sliding inside a housing between at least one diffusion position and one non-fragrant position;
at least one first window made in the slide and intended to receive a source of fragrant molecules;
a second window made in the slide;
in the diffusion position the first window faces a window made in the housing;
in the non-fragrant position the second window faces the window;

these modules are positioned in such a manner that the axes of the windows of the housings of the different modules are aligned;

and in that the rigid structure is designed to cooperate with means for receiving the device in such a manner that these windows are aligned with an air conduit provided in the device.

The modular unit may comprise blocking means designed to block the slides in the non-fragrant position when the unit is not inserted in the device and to unblock these slides when they cooperate with the unblocking means provided on the device.

Such modular units greatly simplify the maintenance procedures for the scent diffusion devices. In fact, the user does not need to access the cartridge but only to substitute one modular unit by another one. Moreover, "thematic" units can be developed and associated with a precise film in such a manner that that the user inserts the appropriate module into the device before viewing the film. The operations are therefore simplified.

We also provide a process for the diffusion of scents making use of a previously cited device and comprising:
  inserting scent cartridges inside the windows of the modules;
  creating a flow of air by means of these means for producing a flow of air, which flow of air traverses the of the windows of the housings;
  presenting at least a first window opposite the window in such a manner that the flow of air traversing the windows also traverses the scent cartridge contained in this first window presented, which diffuses its scent.

The process may further comprise during the use of a cartridge updating an electronic chip associated with the cartridge and comprising at least digital data representative of the use of the cartridge.

It is also provided that several scents are diffused at the same time, requiring:
  either the simultaneously placing of several slides along the air corridor in fragrant position,
  or a very rapid commutation of the slides of the scents to be diffused by the driving means. This rapidity is possible with the technology proposed, namely, the electronic driving of the servomotors.

We also provide a cartridge of materials drenched with volatile fragrant molecules and intended to be inserted into the windows of the previously cited devices. The cartridge has:
  two opposing surfaces designed in such a manner as to allow free passage to a flow of air while holding the materials fast,
  a thickness that is perceptibly less than that of the slide to permit it to freely slide in the housing including when the cartridge is in place in the window of the slide,
  a shape that approximately matches that of the window in such a manner that the totality of the flow of air traversing the window traverses the cartridge,
  a dimension in width that is slightly greater than that of the window in such a manner that the cartridge can be inserted and removed with a slight force by playing on the elasticity of the cartridge.

It is very advantageous to constitute the cartridge to match to the maximum the walls of the window that receives it. In fact, this characteristic, added to the presence of the corridor of air confining the latter ensures that the entire flow of air will cover the perfumed balls, thus offering a high degree of precision of the quantity of perfumes diffused: the balls are spread over 100% of the section of the corridor of air to have a fine control of the diffusion and charge loss in the tubes. In this manner the molecules are torn away in a fine manner: this is similar in particular to the mechanism of fluids in a conduit with an almost constant section. The precision permits in particular an efficient following of the drying state of the drenched cartridges to adapt the flow of air and indicate the need to change the cartridge.

Figure 2:
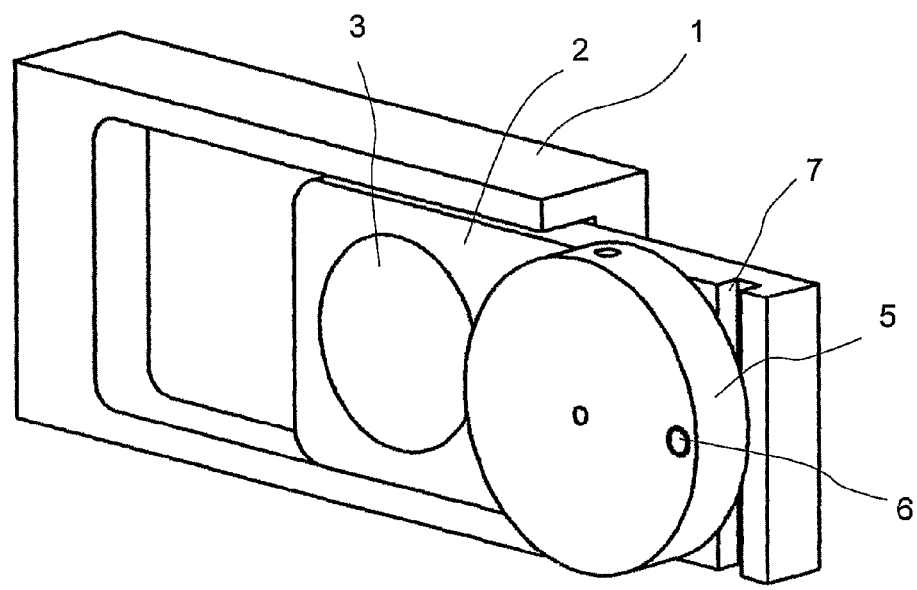
FIG. 2 shows the same diffusion module in a scent-diffusing position.

Referring to FIGS. 1 and 2, each module is composed by a housing 1 inside of which a slide 2 slides. Slide 2 comprises two circular windows 3 and 4 with approximately equal diameters traversing the slide on both parts. Window 3 is intended to receive a removable cartridge 10 containing materials drenched with volatile fragrant molecules. An electric motor 5, e.g., a servomotor, whose stator is integral with housing 1 allows the slide to be moved between two extreme positions. To this end, the rotating part of motor 5 comprises a finger 6 that cooperates with the groove 7 made in slide 2. In one of the two positions of slide 2, qualified in the following as the non-fragrant position and illustrated in FIG. 1, window 4 of slide 2 faces a window 8 with approximately the same diameter made in housing 1. In the other position of slide 2, qualified as the fragrant position and illustrated in FIG. 2, it is window 3 receiving the cartridge of fragrant materials 10 that is located facing window 8 of housing 1.

Housing 1 has in the aggregate a U shape, which facilitates the realization and allows slide 2 to be readily inserted into it.

Figure 3:
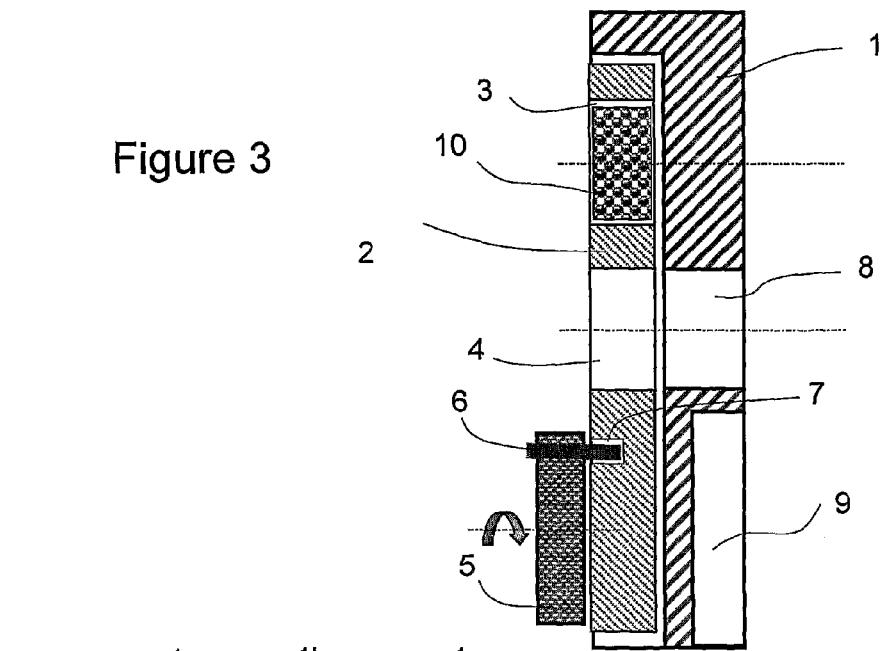
FIG. 3 shows a sectional view of a diffusion module in a non-diffusing position of scent.

FIG. 3 shows a sectional view of a module in a non-fragrant position. Cartridge 10 filled with material drenched with fragrant molecules is in place in window 3 of slide 2. A recess 9 is made in housing 1 to allow the design of a device diffusing several scents by the simple juxtaposing of several modules with motor 5 of a module fitting in recess 9 of the adjacent module.

Figure 4:
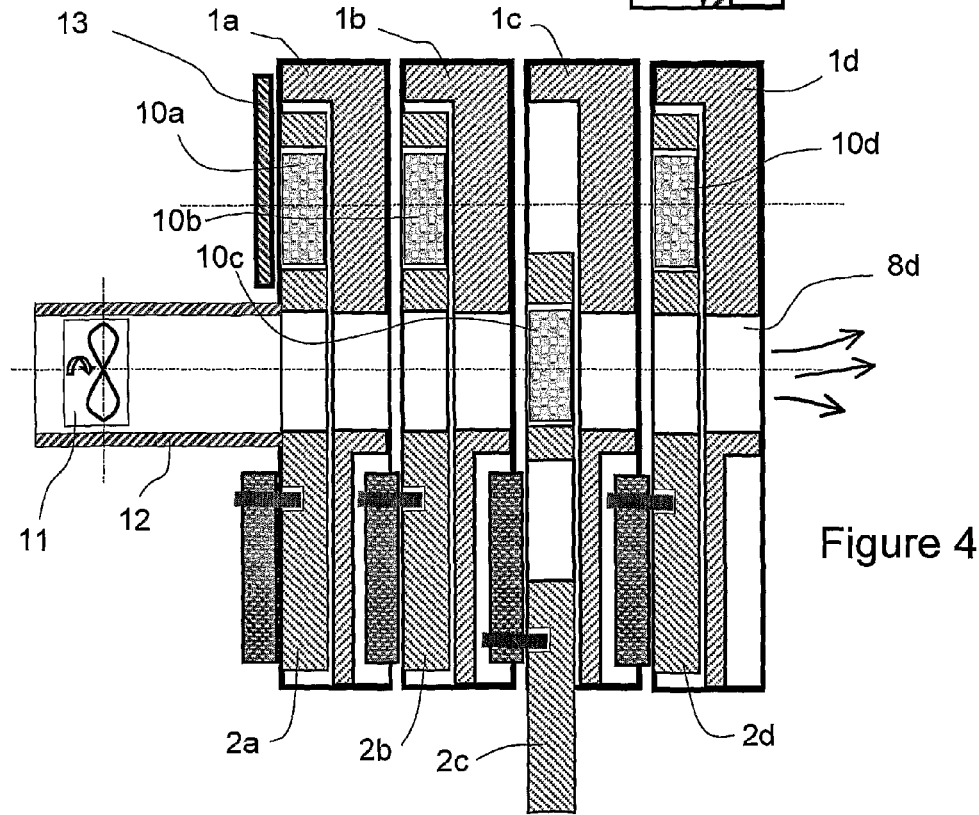
FIG. 4 shows a diffusion device for four scents.

FIG. 4 shows a design of a device composed of four modules designated a, b, c and d. The modules respectively comprise housings 1a, 1b, 1c and 1d and slides 2a, 2b, 2c and 2d. Only module c has its slide in fragrant position, that is, in such a position that its scent cartridge is located facing window 8c of corresponding housing 1c. The three other slides are all in a configuration of non-diffusion of scent because it is their windows 4a, 4b and 4d that are located facing windows 8a, 8b, 8d of corresponding housings 1a, 1b and 1d. Thus, it is the scent of cartridge 10c and only it that is diffused when a flow of air is circulating such as is indicated by the arrows in FIG. 4. This flow of air is created by turbine 11 placed inside a tube 12.

The user selects the scent to be diffused from the four possible ones by actuating motors 5a, 5b, 5c and 5d. The user can also choose not to select any scent by placing all of slides 2a, 2b, 2c and 2d in such a position that none of the cartridges 10a, 10b, 10c, 10d is located facing window 8 of the corresponding housing. Activation of the motors can be controlled by an electronic controller or an electronic port of a classic computer device not shown in figures. Thus, the different scents present in the cartridges are diffused via the same air corridor and exit at the same end.

When slide 2 is in the position of not diffusing a scent, cartridge 10 is closed in such a manner that it is inaccessible to air, which prevents it from drying out in an untimely manner. This closing of the cartridges not being used is readily obtained by juxtaposing the modules in contact with each other with the housing of each module being placed in contact with the housing of the adjacent module. This achieves sufficient tightness while leaving the slides free to change position if the design provides a mechanical play with a small dimension, e.g., on the order of a tenth of a millimeter, between a slide and the housing of the adjacent module. Since module a does not have a neighbor on the face where cartridge 10a is visible, a plate 13 is provided to prevent cartridge 10a from drying out in an untimely manner when slide 2a is in non-fragrant position.

This configuration in four modules is only a design example. We permit conception of devices for which the number of modules can be selected as a function of the number of different scents that are to be diffused.

This number of modules can also be selected as a function of the time necessary for the operation of the device before having to re-drench or replace the scent cartridges. Thus, it is provided that if one of the scents is to be diffused longer than the others, e.g., twice as long, the number of modules is advantageously selected in such a manner as to be able to place twice the number of cartridges of the corresponding scent.

Figure 5:
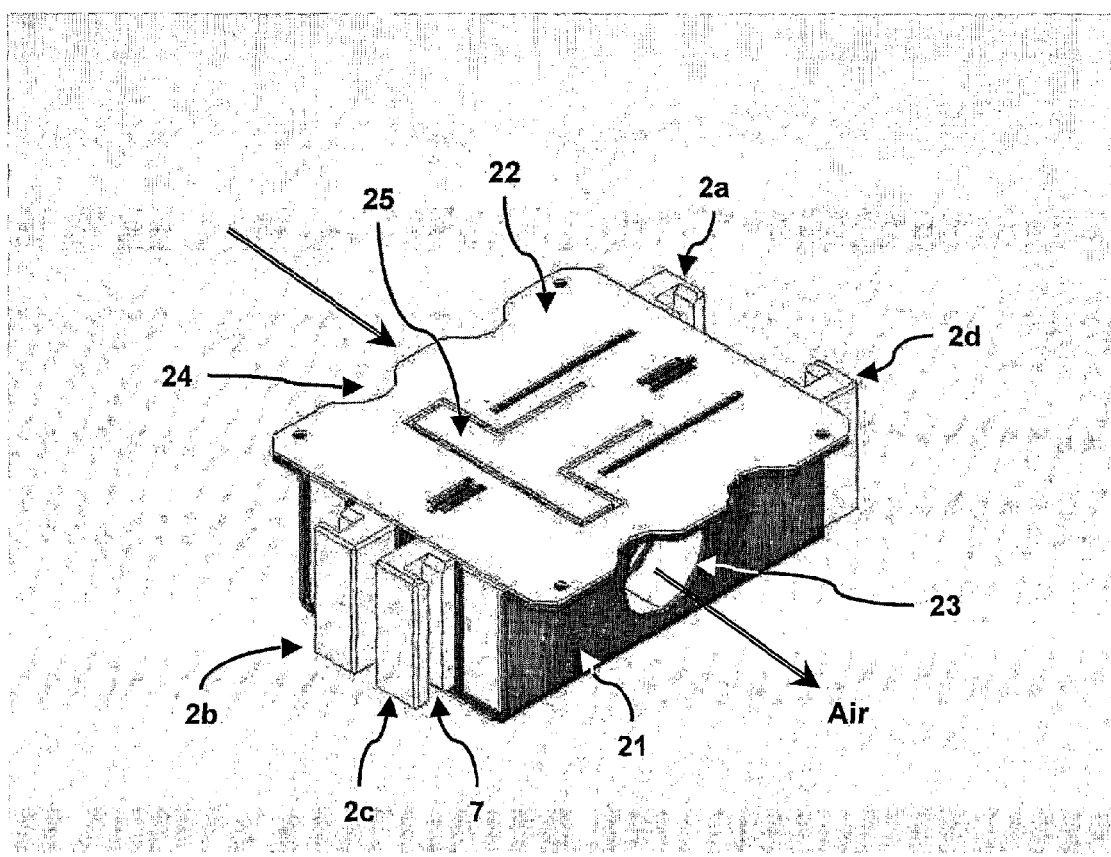
FIG. 5 shows a unit of removable modules.

FIG. 5 shows a design of a replaceable modular unit composed of four modules a, b, c and d housed in a metal casing. The casing is composed of a lower transversal part 21 that is approximately U-shaped and of an upper part 22 with dimensions similar to those of lower part 21 in such a manner as to form together an approximate parallelepiped for receiving the modules. The lateral walls of lower part 2 each comprise an opening 23 corresponding to opening 8 of the modules in order to allow the passage of the flow of air. Lower part 21 can comprise raised edges on the top parts of the "U" to allow the fixation of the upper part 22 as well as notches 24 on these raised edges (and in a symmetric manner on upper part 22) to allow the handling of the device.

The four modules are aligned in such a manner that their openings 8 correspond with openings 23 made in the casing of the device. In a closed position, only grooves 7 of the slides extend out from the casing. To optimize the place occupied by servomotors 5, two modules have their groove 7 on one side of the device and the two other modules on the other side. Referring to FIG. 5, the two extreme slides 2a and 2d have their groove 7 on the same side and facing one another in such a manner that associated servomotors 5a and 5d can be placed in the space left free behind (the side where there are no grooves) the two other modules b and c: servomotor 5a is located approximately behind module b.

Likewise, the grooves of slide modules 2b and 2c extend out from the same side of the casing and are back to back in such a manner that servomotor 5b of slide 2b is approximately arranged behind module a.

Upper part 22 of the casing comprises a tongue 25 machined in the mass in the shape of a "T" placed above the four modules and of which the width is approximately equal to the width of the four modules placed side by side in the casing. The base of the "T" is not machined, thus connecting tongue 25 to the mass of upper part 22. The top part of tongue 25 is free to move slightly up or down.

Figure 6:
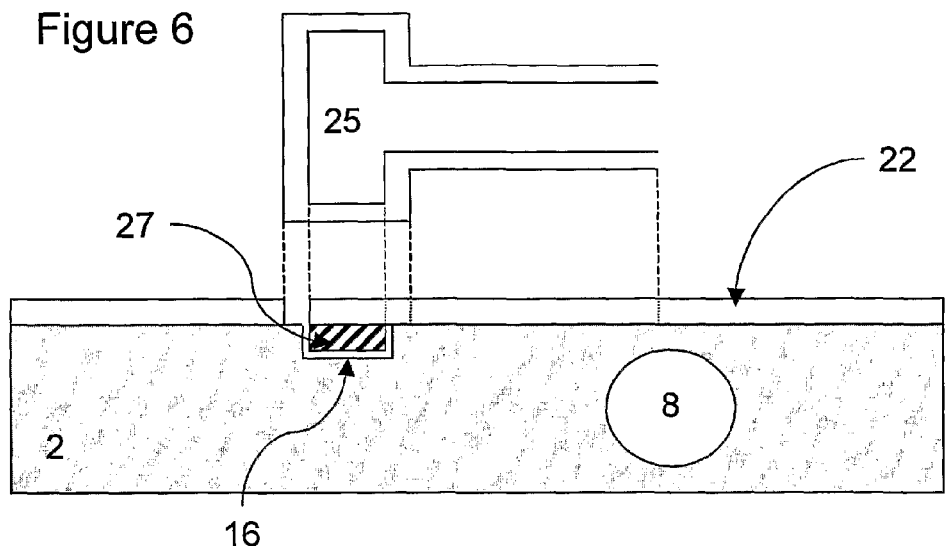
FIGS. 6 to 8 illustrate the blocking mechanisms of the slides.
Figure 7:
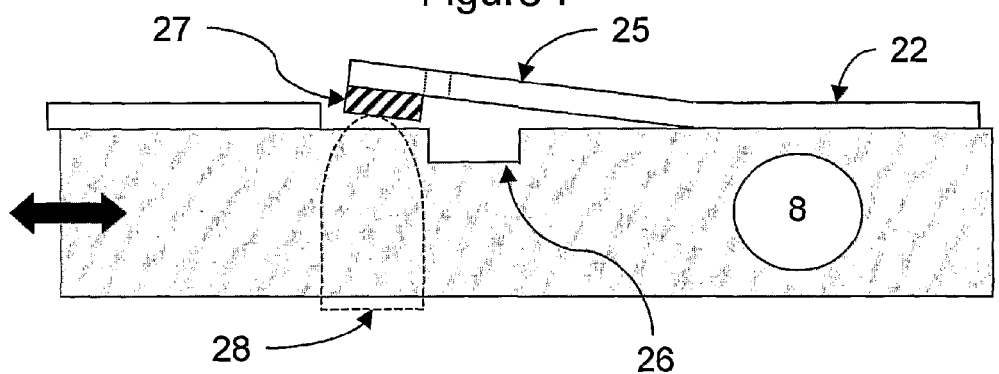

Referring to FIGS. 6 and 7, slides 2 are also provided with a notch 26 on the edge facing tongue 25 in their non-fragrant position and tongue 25 is provided over its width (bar of the "T") with a tappet 27 inside the casing. In closed position illustrated in FIG. 6 tappet 27 of tongue 25 is placed in notch 26 of slide 2, thus blocking it from any opening. In open position illustrated in FIG. 7 tongue 25 is raised up and tapped 27 is no longer in notch 26 of the slide. This latter is then free to slide in the module.

These blocking means 25, 26, 27 are used to keep slides 2 closed in the non-fragrant position when the modular unit is taken out of its placement of use. The open position of the blocking means is obtained by the presence of a metallic "aileron" 28 on the site of the scent diffusion device for receiving this modular unit. Aileron 28, with a slight thickness and a height greater than the height of low part 22 of the casing, slides between slides 2b and 2c in order to come to push tongue 25.

In another aspect, it is envisioned that aileron 28 is mobile and controlled by driving means that block the slides when the modular unit is not used (not inserted in the diffusion device) and frees them when, e.g., the device is placed under voltage.

Figure 8:
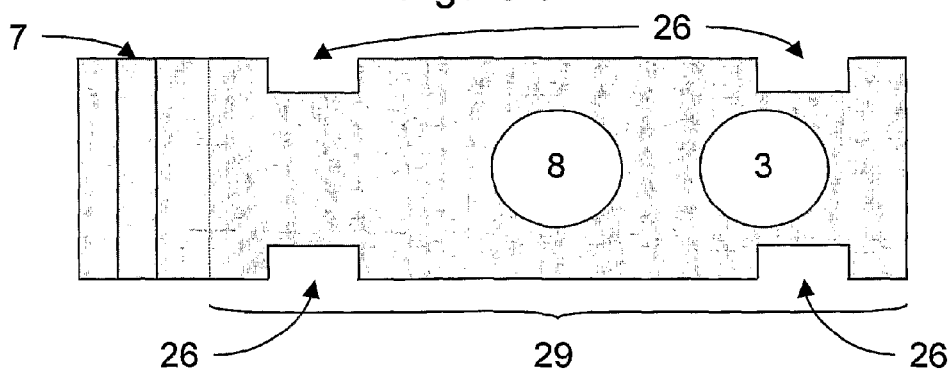

In view of the dissymmetry (blocking notch, distance means of blocking-groove, . . . ) of the modular unit proposed in FIG. 5, it is advantageous to supply a single slide that can be used for all the modules. FIG. 8 shows a slide solution with window 8 at the middle of part 29 received by the casing of the modular unit, one window 3 for receiving the cartridge situated on the side opposite groove 7 and four notches 26 in the upper and lower edges of the slide, which notches are symmetrical with each other in part 29 to face tongue 25 whatever the direction of the introduction of the slide into the module is.

In a more sophisticated structure, the slide comprises several windows 3, which permits several scent cartridges to be placed in them. In this case, the elements of the modules and especially means 5 are adapted in such a manner as to be able to position one or the other of windows 3 as well as a window 4 facing window 8 of housing 1.

Figure 9:
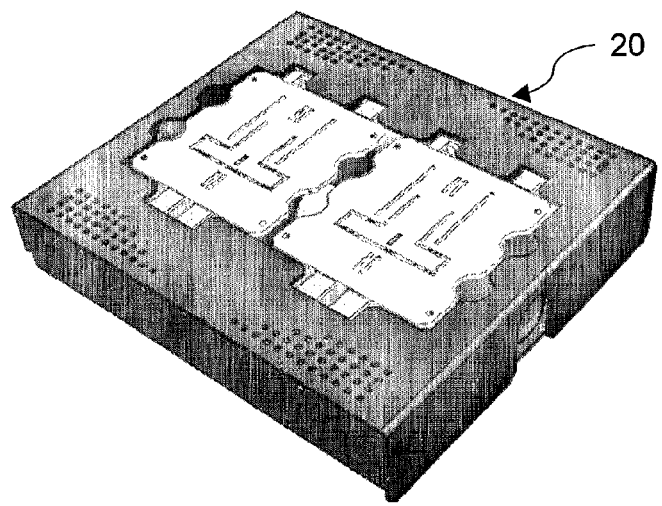
FIG. 9 shows a three-quarter view of the scent diffusion device.
Figure 10:
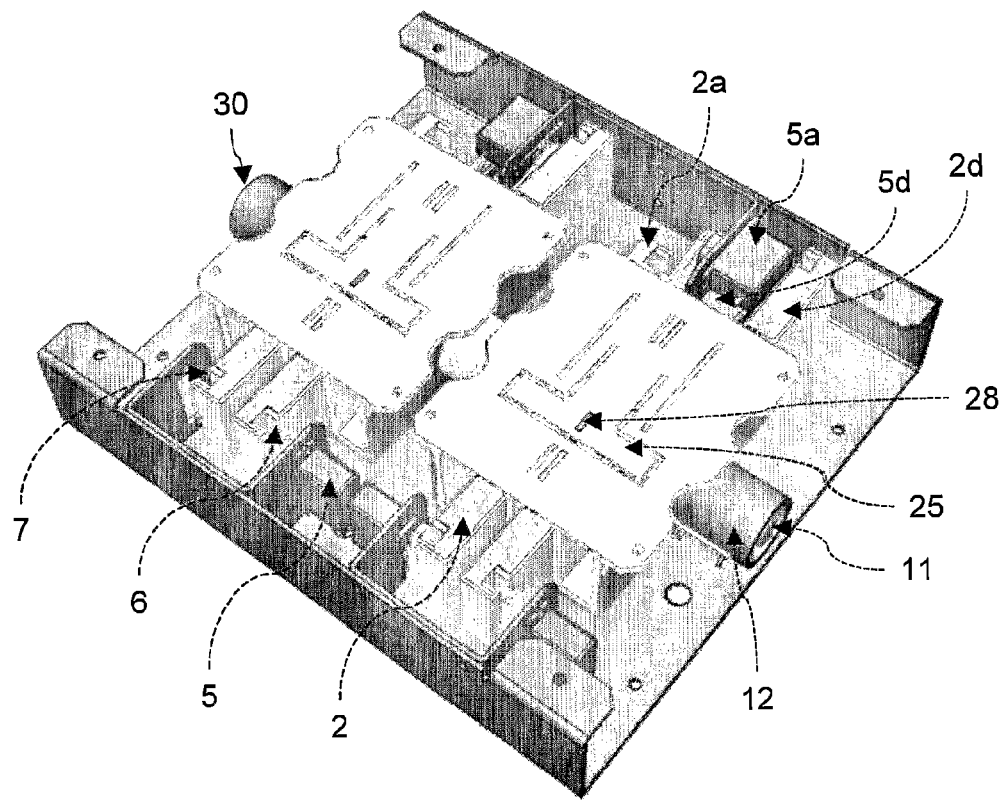
FIG. 10 shows the same device with the cover removed, showing the internal architecture of the device.

FIGS. 9 and 10 show a design of the scent diffusion device for receiving two modular units of four modules previously described in connection with FIG. 5. The apparatus comprises a cover 20 provided with an opening and with notches for allowing placement and withdrawal of the two blocks of modules. Note that the shape of the opening only permits withdrawal of the blocks if slides 2 are all in non-fragrant position, that is to say, folded back to the maximum inside housings 1.

The two modular units (blocks) and their inner modules are aligned in such a manner that their openings 8 correspond with turbine 11, the tube/airway 12 and the device outlet 30. During insertion of the modular units, ailerons 28 raise tongue 25, allowing slides 2 to slide freely.

Servomotors 5a and 5d situated behind modules b and c for actuating slides 2a and 2d are arranged on one another.

This scent diffusion device allows the number of scents that can be driven to be very distinctly increased by juxtaposing several modular units.

We also provide a process of diffusing scents using one of the previously described devices. This process includes inserting scent cartridges 10 inside windows 3 of the modules; creating a flow of air by electric turbine 11, which flow of air traverses the set of windows 8 of housings 1; and presenting at least one window 3 in front of window 8 in such a manner that the flow of air traversing windows 8 also traverses scent cartridge 10 contained in the presented window 3, which diffuses its scent.

We also provide a removable cartridge 10 containing materials drenched with volatile fragrant molecules and intended to be inserted in windows 3 of the modules described above. This cartridge comprises in particular:
  two opposing surfaces designed in such a manner as to allow free passage to a flow of air while holding the materials fast,
  a thickness that is perceptibly less than that of the slide 2 to permit it to freely slide in the housing 1 including when the cartridge 10 is in place in the window 3 of the slide 2,
  a shape that approximately matches that of the window 3 in such a manner that the totality of the flow of air traversing the window 3 traverses the cartridge 10, a dimension in width that is slightly greater than that of the window 3 in such a manner that the cartridge 10 can be inserted and removed with a slight force by playing on the elasticity of the cartridge 10.

The cartridge is also magnetized by a rigid structure surrounding the drenched material and fitting the shape of window 3. The rigid magnetized structure allows a ready installation of cartridge 10 and maintaining the latter in window 3.

The materials used for such cartridges are typically of a polymeric nature, e.g., PEBAX (Polyester Block Amides of the ATOFINA company—commercial names).

In a particular structure, electronic chips for reading by contact are integrated in the modules or in the modular units. The device receiving the modules comprises contact readers of electronic chips, which readers face the chips of the modules when the latter are introduced into the scent diffusion device.

The chips make it possible to find out a large amount of information used in the management of the modules:

date when the module was loaded on the device;

scent in the module/modules;

the location of the scents in a module unit;

the service life, duration of use.

According to the structure selected, a chip can be placed on the lower face of the module. At each loading of a new module in the device the diffusion device reads the chip (the information of the new inserted module) and is re-parameterized with the information of the new module loaded (updating of parameters, for example).

According to another structure, the chip is present on the lower edge of housing 1 of each of modules a, b, c and d, and the lower face of the casing then has four openings at the level of the chips of the modules to allow the reading by the readers of the apparatus. The chip can be pre-parameterized during its designing and the corresponding module is then only loaded into the device. The chip can also be parameterized by the installer and/or automatically by the readers of the apparatus receiving the device during the loading of the module by teaching, e.g., the loading date and the location of the module concerned.

The data present in the chip can therefore by used by the software for driving the devices for actuating the correct slide according to the encoding in the corresponding multimedia flow with which a scent is to be associated. Managing the modules is improved in the presence of the chips:

the knowledge of the loading date allows the user to avoid that the cartridge becomes too old;

information about the time of use of a cartridge simultaneously allows adapting the flow of air (to take account of the depletion of molecules in the time of the cartridge) and an indication that the cartridge is no longer effective (total time of use exceeded);

the driving software uses the nature of the scents of the modules and the time of use of their cartridge with monograms contained in a database in order to evaluate the consumption of scent molecules during use and non-use of the cartridges;

when a device is introduced into a driving apparatus, typically a multi-sensory animated table, the detection of the scents present and their location is realized automatically; the information is sent back to the driving software, that can actuate the correct servomotors in a reliable manner.

The invention claimed is:

1. A scent diffusion device comprising:
    means for generating a flow of air;
    an outlet, the generating means and outlet defining a path for the flow of air therebetween;
    a plurality of scent diffusion modules comprising:
        a slide moveable by sliding inside a housing between at least one diffusion position and a non-fragrant position;
        at least one first window in the slide intended to receive a source of fragrant molecules;
        a second window in the slide;
        wherein, in the diffusion position, the first window faces a window in the housing and in the non-fragrant position, the second window faces the window in the housing, and wherein the modules are positioned such that window axes of the housings of different modules are aligned on the path; and
    means permitting the slides to be brought individually into one of the positions, the flow of air successively traversing the windows of the housings, the first window and the second window of the slides according to positions of the latter.

2. The scent diffusion device according to claim 1, wherein the path has walls forming a corridor of air and windows of the modules are aligned in the air corridor.

3. The scent diffusion device according to claim 2, wherein the windows have substantially the dimension of the section of the air corridor and are oriented substantially perpendicularly to the axis of the corridor.

4. The scent diffusion device according to claim 1, wherein the modules are juxtaposed housing against housing.

5. The scent diffusion device according to claim 1, wherein the means permitting displacement of the slides are activated by an electric control part.

6. The scent diffusion device according to claim 1, further comprising a plurality of means permitting movement of the slides, and each of the plurality of means is individually associated with one of the plurality of modules for the diffusion of scents.

7. The scent diffusion device according to claim 6, wherein the means permitting movement of the slide is a servomotor whose stator is integral with the housing and whose rotor is integral with an eccentric finger that cooperates with a groove formed in the slide.

8. The scent diffusion device according to claim 1, wherein each of the housings has in the aggregate a U shape inside of which the slide associated with the housing is inserted and slides.

9. The scent diffusion device according to claim 1, wherein each module not having a neighbor on the face where the cartridge is visible comprises a plate suitable for shutting a source in a manner inaccessible to air when the slide is in a position that the second window faces the window of the housing.

10. The scent diffusion device according to claim 1, wherein at least one module is removable and comprises means for blocking the slides in the non-fragrant position when it is not inserted in the device, and the device comprises means for unblocking the blocking means when the removable module is inserted in the device.

11. The scent diffusion device according to claim 1, wherein the modules comprise means for the storage of data comprising at least digital data representative of information concerning sources of fragrant molecules that they contain, and further comprises means for reading the data storage means, which reading means are connected to an electronic card for driving the device.

12. The scent diffusion device according to claim 1, wherein a source of fragrant molecules is a removable cartridge drenched with fragrant molecules.

13. The scent diffusion device according to claim 12, wherein the cartridge comprises data storage means comprising at least digital data representative of scent contained in the cartridge, and further comprises means for reading the data storage means, which reading means are connected to an electronic card for driving the device.

14. The scent diffusion device according to claim 1, wherein the means for generating a flow of air are selected from a ventilator and an air turbine.

15. The scent diffusion device according to claim 1, further comprising means for accelerating flow of air arranged in the air corridor and driven by an electronic card for driving the device.

16. The scent diffusion device according to claim 1, further comprising means for adapting output of flow of air at an outlet of the air corridor.

17. The scent diffusion device according to claim 1, wherein the slide of at least one module further comprises at least a third window designed to receive a second source of fragrant molecules, which means allows the slide to be moved and is then suitable for bringing the slide to one of at least three positions corresponding to alignment of a window of the slide with a window of the housing.

18. A modular unit for a device according to claim 1, comprising $2^i$ scent diffusion modules (i is a whole number from 1 to 3) arranged in a rigid structure with each module comprising:
   a slide that can move by sliding inside a housing between at least one diffusion position and one non-fragrant position;
   at least one first window in the slide and adapted to receive a source of fragrant molecules;
   a second window in the slide;
   wherein, in the diffusion position, the first window faces a window in the housing and in the non-fragrant position, the second window faces the window;
   wherein the modules are positioned in such a manner that axes of the windows of the housings of the different modules are aligned; and
   the rigid structure cooperates with means for receiving the device in such a manner that the windows are aligned with an air conduit.

19. The modular unit according to claim 18, comprising blocking means designed to block the slides in the non-fragrant position when the unit is not inserted in the device and to unblock the slides when they cooperate with the unblocking means.

20. A process for diffusion of scents using a device in accordance with claim 1, comprising:
   inserting scent cartridges inside the windows of the modules,
   creating a flow of air with the means for producing a flow of air, which flow of air traverses the set of windows of the housing, and
   placing at least a first window in front of the window such that flow of air traversing the windows also traverses the scent cartridge contained in the first window, which diffuses its scent.

21. The process according to claim 20, further comprising during the use of a cartridge, updating an electronic chip associated with the cartridge and comprising at least digital data representative of use of the cartridge.

22. A cartridge or materials drenched with volatile fragrant molecules, adapted to be inserted in the windows of devices in accordance with claim 1, comprising:
   two opposing surfaces designed to allow free passage to a flow of air while holding the materials,
   a thickness that is perceptibly less than that of the slide to permit the slide to freely slide in the housing including when the cartridge is in place in the window of the slide,
   a shape that substantially matches that of the window such that the totality of the flow of air traversing the window traverses the cartridge,
   a dimension in width that is slightly greater than that of the window such that the cartridge can be inserted and removed with a slight force by the elasticity of the cartridge.

23. e cartridge according to claim 22, further comprising a rigid structure surrounding the drenched material and being magnetized to allow a ready installation of the cartridge and maintaining the cartridge in the window.

\* \* \* \* \*